(12) United States Patent
Schwartz

(10) Patent No.: US 8,062,894 B2
(45) Date of Patent: Nov. 22, 2011

(54) GENERATION OF FLUORESCENT MICROBEAD CELLULAR SURROGATE STANDARDS

(76) Inventor: Abraham Schwartz, San Juan, PR (US)

( * ) Notice: Subject to any disclaimer, the term of this patent is extended or adjusted under 35 U.S.C. 154(b) by 0 days.

(21) Appl. No.: 12/367,876

(22) Filed: Feb. 9, 2009

(65) Prior Publication Data

US 2010/0203642 A1 Aug. 12, 2010

(51) Int. Cl.
  *G01N 21/64* (2006.01)
  *G01N 21/00* (2006.01)
  *G02B 5/22* (2006.01)
(52) U.S. Cl. ........ 436/86; 250/458.1; 359/888; 359/885
(58) Field of Classification Search ................ 436/8, 86; 523/202, 200, 1; 250/458.1; 359/888, 885
  See application file for complete search history.

(56) References Cited

U.S. PATENT DOCUMENTS

| | | | | | |
|---|---|---|---|---|---|
| 4,698,262 A | * | 10/1987 | Schwartz et al. | ............. | 428/402 |
| 4,699,826 A | * | 10/1987 | Schwartz et al. | ............. | 428/402 |
| 4,699,828 A | * | 10/1987 | Schwartz et al. | ............. | 428/402 |
| 4,714,682 A | * | 12/1987 | Schwartz | ......................... | 436/10 |
| 4,774,189 A | * | 9/1988 | Schwartz | ......................... | 436/10 |
| 4,828,984 A | * | 5/1989 | Schwartz | ..................... | 435/7.21 |
| 4,857,451 A | * | 8/1989 | Schwartz | ..................... | 435/7.24 |
| 4,868,126 A | * | 9/1989 | Schwartz | ......................... | 436/10 |
| 4,918,004 A | * | 4/1990 | Schwartz | ..................... | 435/7.24 |
| 5,073,498 A | * | 12/1991 | Schwartz et al. | ................. | 436/8 |
| 5,380,190 A | * | 1/1995 | Kumagai | .......................... | 431/1 |
| 5,380,663 A | * | 1/1995 | Schwartz et al. | ............... | 436/10 |
| 2003/0055233 A1 | * | 3/2003 | Krull | ............................. | 536/23.1 |
| 2007/0236796 A1 | * | 10/2007 | Putnam et al. | ................ | 359/566 |

OTHER PUBLICATIONS

Siwick et al., Polymeric nanostructured material for high-density three dimensional optical memory storage, Nov. 15, 2001, Journal of Applied Physics, vol. 90, No. 10, pp. 5328-5334.*

* cited by examiner

*Primary Examiner* — Christine T Mui
(74) *Attorney, Agent, or Firm* — Hoglund & Pamias, PSC; Roberto J. Rios

(57) ABSTRACT

A method of producing microbead populations that mimics the fluorescence intensity profile distribution of fluorescent biological cells so that they may be used a standard for flow cytometry.

12 Claims, 9 Drawing Sheets

FIG. 9

| Channel Number | Number of Events |
|:---:|:---:|
| 1 | 0 |
| 2 | 0 |
| 3 | 0 |
| 4 | 0 |
| 5 | 0 |
| 6 | 0 |
| 7 | 0 |
| 8 | 1 |
| 9 | 2 |
| 10 | 4 |
| 11 | 5 |
| 12 | 7 |
| 13 | 11 |
| 14 | 19 |
| 15 | 16 |
| 16 | 13 |
| 17 | 8 |
| 18 | 5 |
| 19 | 2 |
| 20 | 1 |
| 21 | 0 |
| 22 | 0 |
| 23 | 0 |
| 24 | 0 |
| 25 | 0 |

FIG. 10

| Channel Number | Inverted Number of Events |
|---|---|
| 1 | 19 |
| 2 | 19 |
| 3 | 19 |
| 4 | 19 |
| 5 | 19 |
| 6 | 19 |
| 7 | 19 |
| 8 | 18 |
| 9 | 17 |
| 10 | 15 |
| 11 | 14 |
| 12 | 12 |
| 13 | 8 |
| 14 | 0 |
| 15 | 3 |
| 16 | 6 |
| 17 | 11 |
| 18 | 14 |
| 19 | 17 |
| 20 | 18 |
| 21 | 19 |
| 22 | 19 |
| 23 | 19 |
| 24 | 19 |
| 25 | 19 |

FIG. 11

| Channel Number | Percentiles |
|:---:|:---:|
| 1 | 100 |
| 2 | 100 |
| 3 | 100 |
| 4 | 100 |
| 5 | 100 |
| 6 | 100 |
| 7 | 100 |
| 8 | 95 |
| 9 | 90 |
| 10 | 80 |
| 11 | 75 |
| 12 | 65 |
| 13 | 40 |
| 14 | 0 |
| 15 | 15 |
| 16 | 30 |
| 17 | 60 |
| 18 | 75 |
| 19 | 90 |
| 20 | 95 |
| 21 | 100 |
| 22 | 100 |
| 23 | 100 |
| 24 | 100 |
| 25 | 100 |

FIG. 12

| Channel Number | Sorted Percentiles |
|---:|---:|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 95 |
| 14 | 95 |
| 15 | 90 |
| 16 | 90 |
| 17 | 80 |
| 18 | 75 |
| 19 | 75 |
| 20 | 65 |
| 21 | 60 |
| 22 | 40 |
| 23 | 30 |
| 24 | 15 |
| 25 | 0 |

GENERATION OF FLUORESCENT MICROBEAD CELLULAR SURROGATE STANDARDS

FIELD OF THE INVENTION

The present invention relates to microbead populations, and more particularly to a method of producing microbead populations that mimic the fluorescence intensity profile distribution of fluorescent biological cells so that they may be used as a standard for flow cytometry.

BACKGROUND OF THE INVENTION

Microbeads have been used as surrogate cell standards in various biological fields for many years. This is especially true since highly uniform microbeads, in the 2-15 micron diameter range, have been first produced by John Ugelstad. As a particle surrogate, polymeric microbeads have high physical stability, as well as the ability to be labeled with the same fluorochromes and dyes as used to label biological cells. Moreover, a great deal of work has been addressed to make microbeads useful as fluorescent particle reference and quantitative standards. When labeled with such fluorochromes and dyes, these microbeads exhibit many of characteristics as labeled biological cells, as determined by instrumentation of at least one of flow cytometry. Specifically, fluorochrome labeled microbeads appear to have similar forward and side light scatter properties, as well as similar spectral and intensity fluorescent properties as biological cells.

However, the fluorescence intensity distribution profile of microbeads and biological cells labeled with the same fluorochrome can appear vastly different. For example human lymphocytes labeled with a fluorescently conjugated CD8 antibody, has a fluorescence intensity distribution, as shown in FIG. 1. This distribution is really the combined response of CD8 suppressor cells, the tall intense population on the right end of the distribution, and CD8 cyto-toxic cells, the low widely spread population to the left of the CD8 suppressor cells.

Much effort in the manufacture of microbeads is focused on producing highly uniform physical properties, of at least one of size, volume and fluorescence intensity. Such populations are highly sort after for use as size and fluorescence standards in fields of at least one of flow cytometry and fluorescence microscopy. Normally, these methods of production ensure that fluorochromes or dyes are taken up by the microbeads in a highly uniform fashion resulting in a very tight fluorescence intensity distribution, as shown in FIG. 2.

However, it stands to reason that, the closer the standards mimic analyte being measured, the better the instrument performance can be evaluated to measure the analyte. An example to illustrate this may be found when counting CD8 labeled lymphocytes. If a fluorescent population of microbeads with the usual tight intensity distribution is used as the count standard, the standard is only determining the ability of the instrument to detect and count events in a narrow range of the intensity scale, as shown in FIG. 2. However, as seen in FIG. 1, the intensity distribution of CD8 labeled lymphocytes cover a wide non-uniform intensity range. Although highly uniform intensity microbeads have served the biology and medical communities as cellular surrogates and standards well for a long time, the ability of microbeads that more closely resemble the intensity distributions of biological cells would be very welcome to these communities.

SUMMARY OF THE INVENTION

The present invention solves this need by providing a method to manipulate a population of microbeads labeled with a fluorescent material or optical dye so that it mimics the fluorescent intensity distribution of a biological cell population labeled with the same fluorescent material or dye. This may be accomplished by a number of ways which include, but are not limited to at least one of: 1) mixing microbead populations of different intensities and uniformities, 2) manipulating the method of addition of the fluorescent material or 3) performing precision photo bleaching of a uniform population of microbeads.

To achieve the foregoing and other advantages, the present invention, briefly described, provides method to manipulate a population of microbeads labeled with a fluorescent material or dye so that it mimics the fluorescent intensity distribution of a biological cell population labeled with the same fluorescent material or optical dye, by mixing different uniform populations of microbeads labeled with a fluorescent material in specific proportions, the overall fluorescent intensity pattern of the mixture can result in the same intensity pattern of the a cell population of interest labeled with the same material.

The intensity profile of a labeled cell population is also mimicked by carefully adjusting the physical parameters during the dying or polymerization procedure of the microbeads. Namely, adjusting the rate of dye addition, the stirring conditions and varying concentrations of the fluorescent material during the process.

Further another method of adjusting a fluorescence intensity profile of a microbead population is accomplished using a process referred to as photo bleaching. That is, when fluorescent materials are exposed to strong light, especially wavelengths within their absorption spectra, the fluorescent molecules undergo destruction at some intrinsic rate, resulting in lower fluorescent intensity of the population as a whole. However, if different portions of the uniform population of microbeads are photobleached in a precise and predetermined manner at specific rates, the resulting intensity profile of the microbead population can be made to mimic the intensity profile of the labeled biological cells. This process is referred to as precision photo bleaching.

Numerous objects, features and advantages of the present embodiment of the invention will be readily apparent to those of ordinary skill in the art upon a reading of the following detailed description of presently preferred, but nonetheless illustrative, embodiments of the invention when taken in conjunction with the accompanying drawings. In this respect, it is to be understood that the embodiment of the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present embodiment of the invention.

BRIEF DESCRIPTION OF THE DRAWINGS

FIG. 9 shows data from a list mode file indicating the number of events in each intensity channel of the histogram.

FIG. 10 shows data from FIG. 9 that has been inverted.

FIG. 11 shows data from FIG. 10 that has been normalized to a density percentage.

FIG. 12 shows normalized data from FIG. 11 that has been sorted.

DESCRIPTION OF THE INVENTION

This specification and the accompanying figures disclose the preferred embodiment as example of the invention. The drawings illustrated in the figures are not to scale and are only intended to serve as illustrating examples of the invention. The invention is not intended to be limited to the embodiment illustrated. Numerous modifications, changes, variations, substitutions and equivalents will be apparent to those skilled in the art without departing from the spirit and scope of the present invention.

Figure 8:
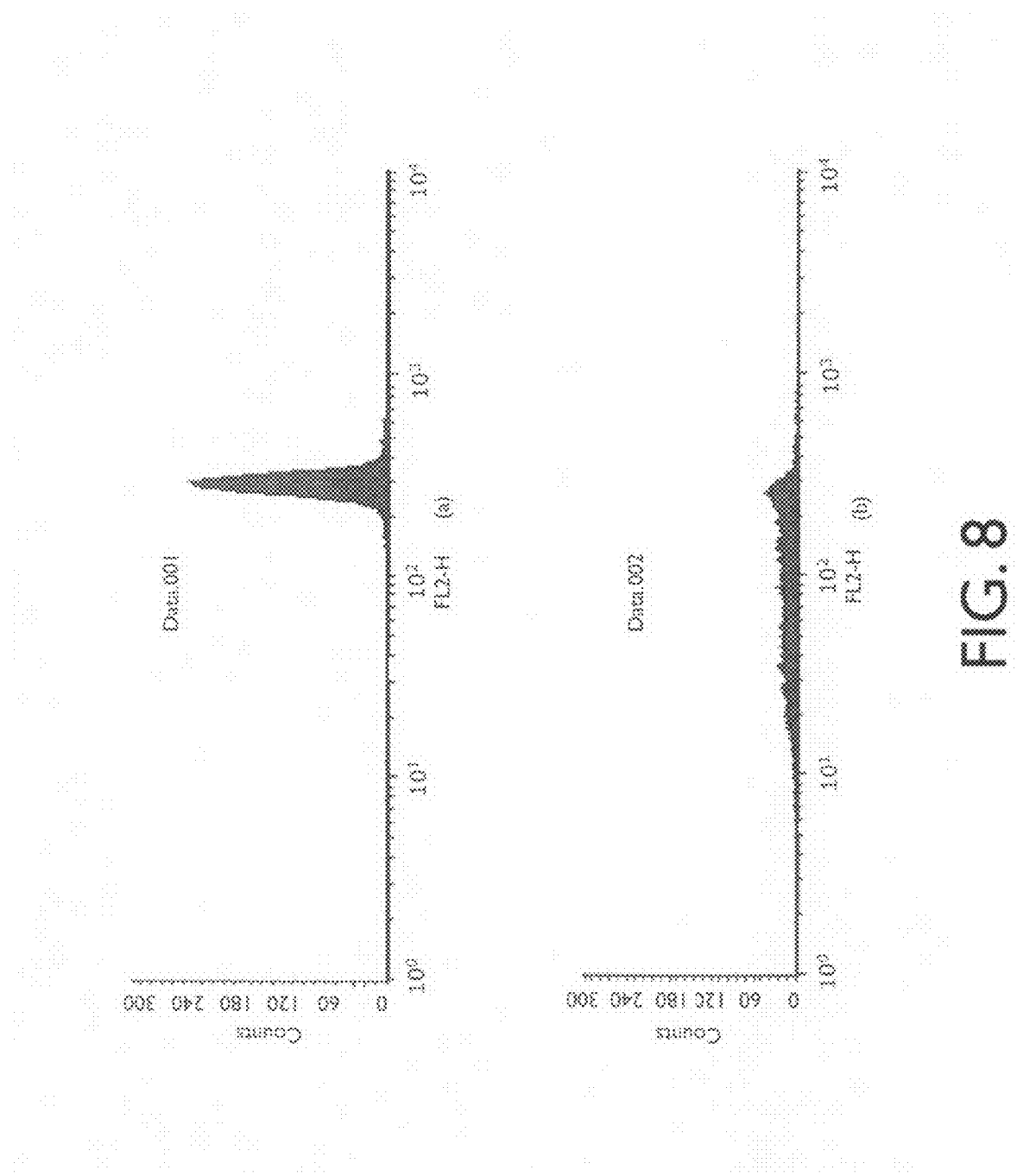
FIG. 8 shows fluorescence intensity profiles of a microbead population (a) before and (b) after photo bleaching through a optical density gradient.

Referring now to FIG. 8, the preferred embodiment of the invention involves a method, an algorithm, and a precision photo bleaching apparatus for the production of microbeads that provide specific fluorescence intensity profiles to microbead populations that mimic fluorescently labeled biological cells.

In general, the microbeads are uniformly spread over a given area. This may be done by filling a shallow flat-bottomed container and allowing the microbeads to settle uniformly onto the bottom of the container. An optical density gradient is placed over these microbeads and a light source of optimal wavelengths is directed through density gradient onto the uniform layer of microbead. The intensity and length of time the light is directed onto the microbeads controls the overall fluorescence intensity of the population, however, the intensity profile within the microbead population will retain an intensity profile across the illuminated area inversely proportional to the density gradient covering the microbeads.

Figure 1:
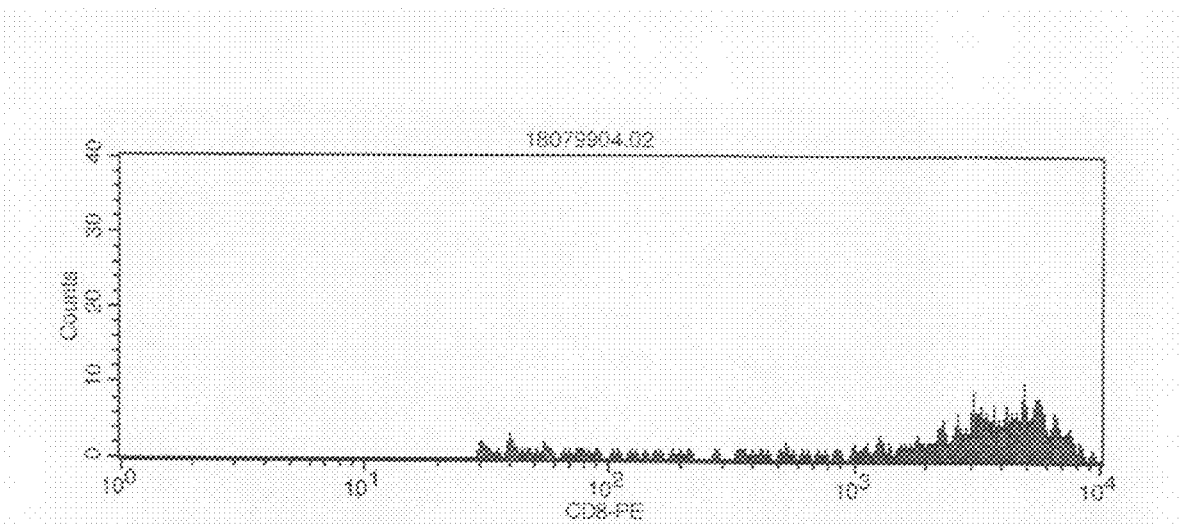
FIG. 1 shows a fluorescence intensity distribution of CD8 labeled with a fluorescent CD8 antibody.
Figure 2:
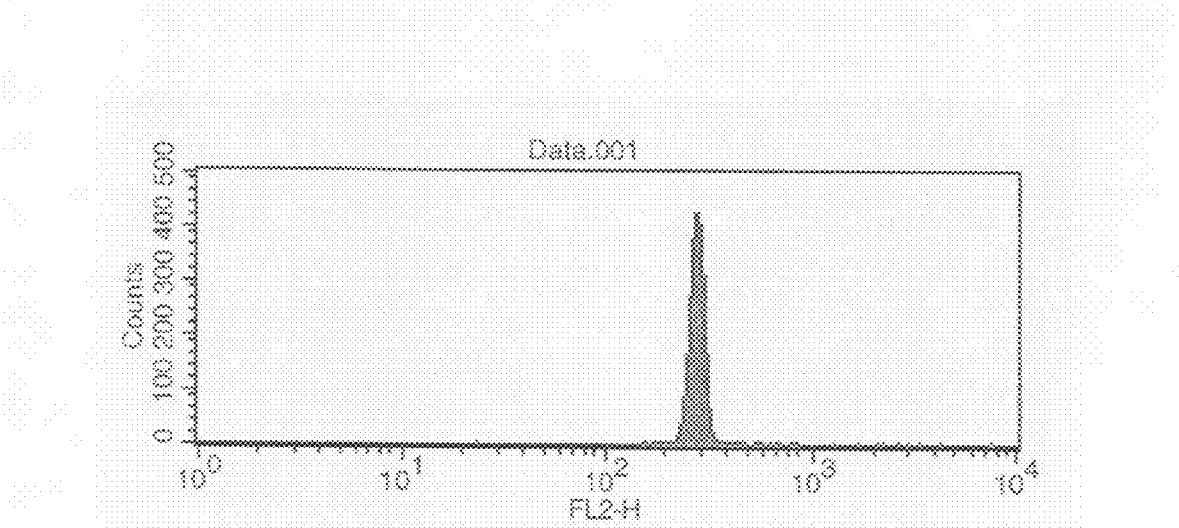
FIG. 2 shows a fluorescence intensity distribution microbeads labeled with the same fluorochrome as bound to the CD8 antibody in FIG. 1.
Figure 3:
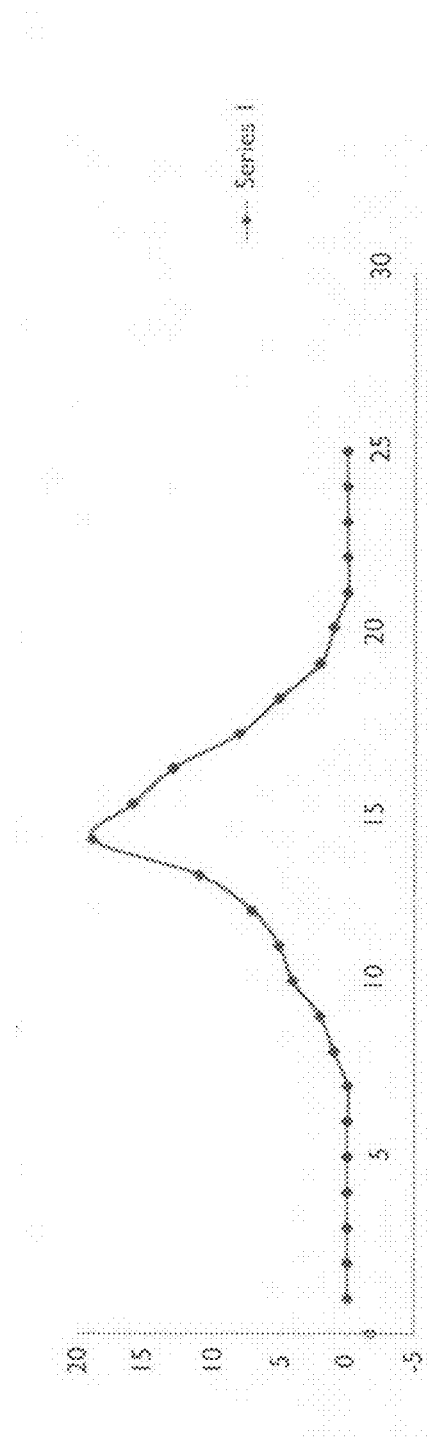
FIG. 3 shows a plot of an intensity distribution from FIG. 9
Figure 4:
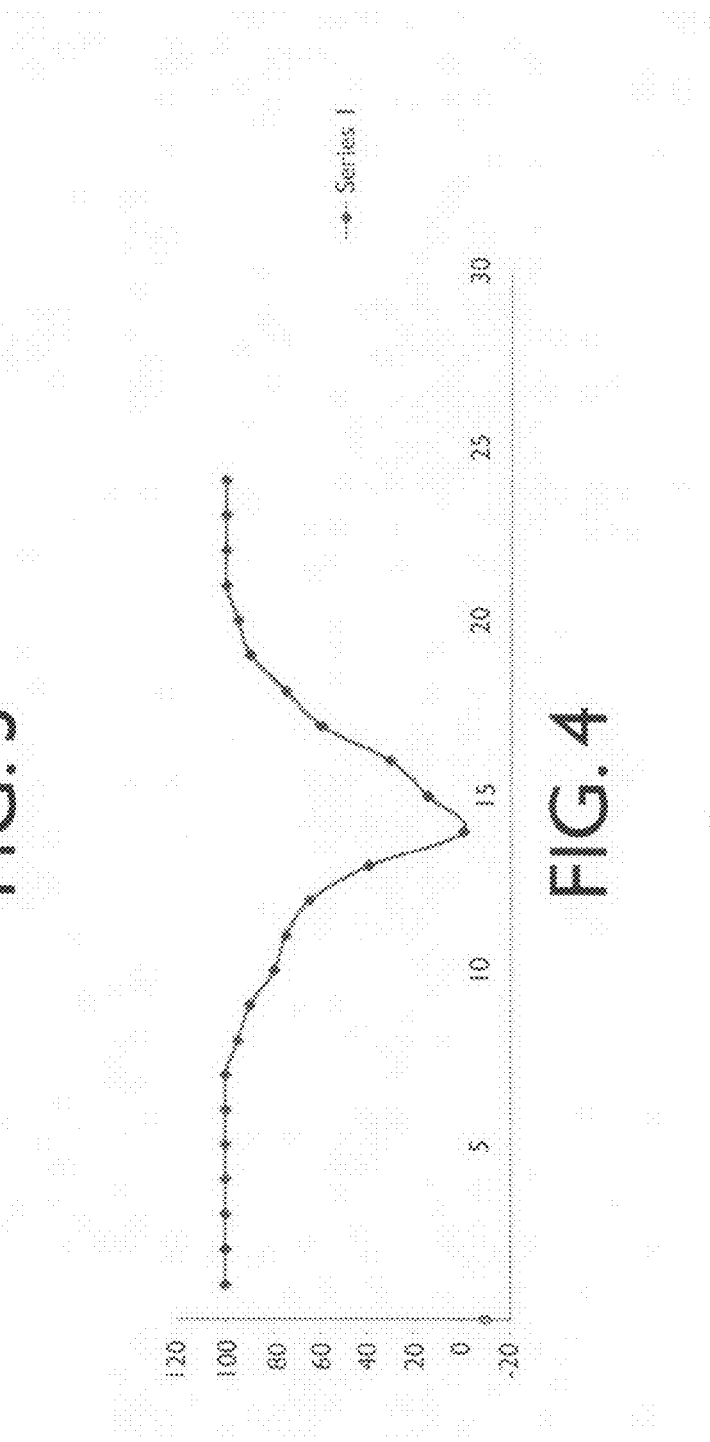
FIG. 4 shows a plot of the inverted intensity distribution percentile from FIG. 10.
Figure 6:
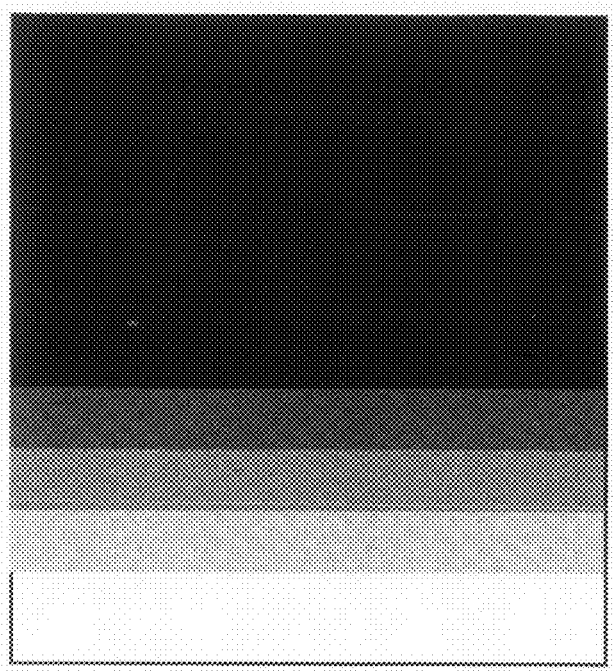
FIG. 6 shows the density gradient used to perform precision photo bleaching.
Figure 5:
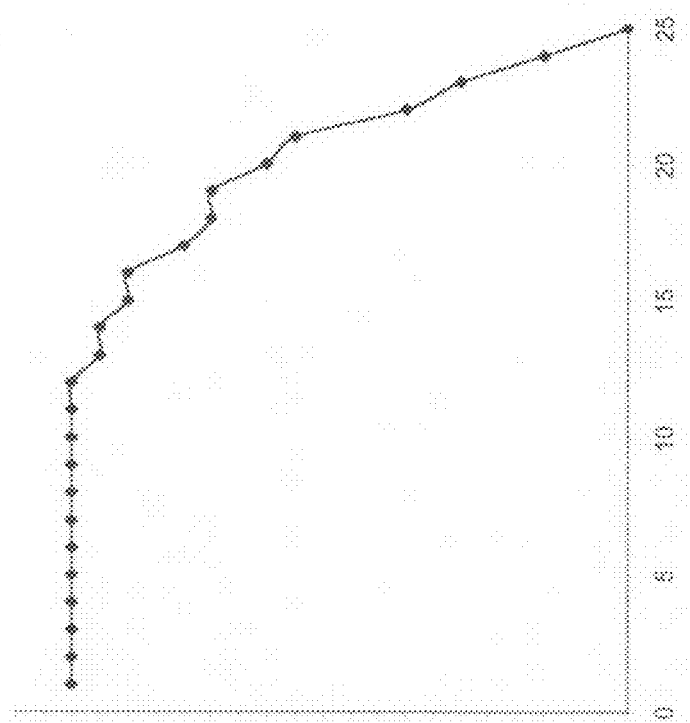
FIG. 5 shows a plot of the sorted inverted intensity distribution percentile from FIG. 11.
Figure 7:
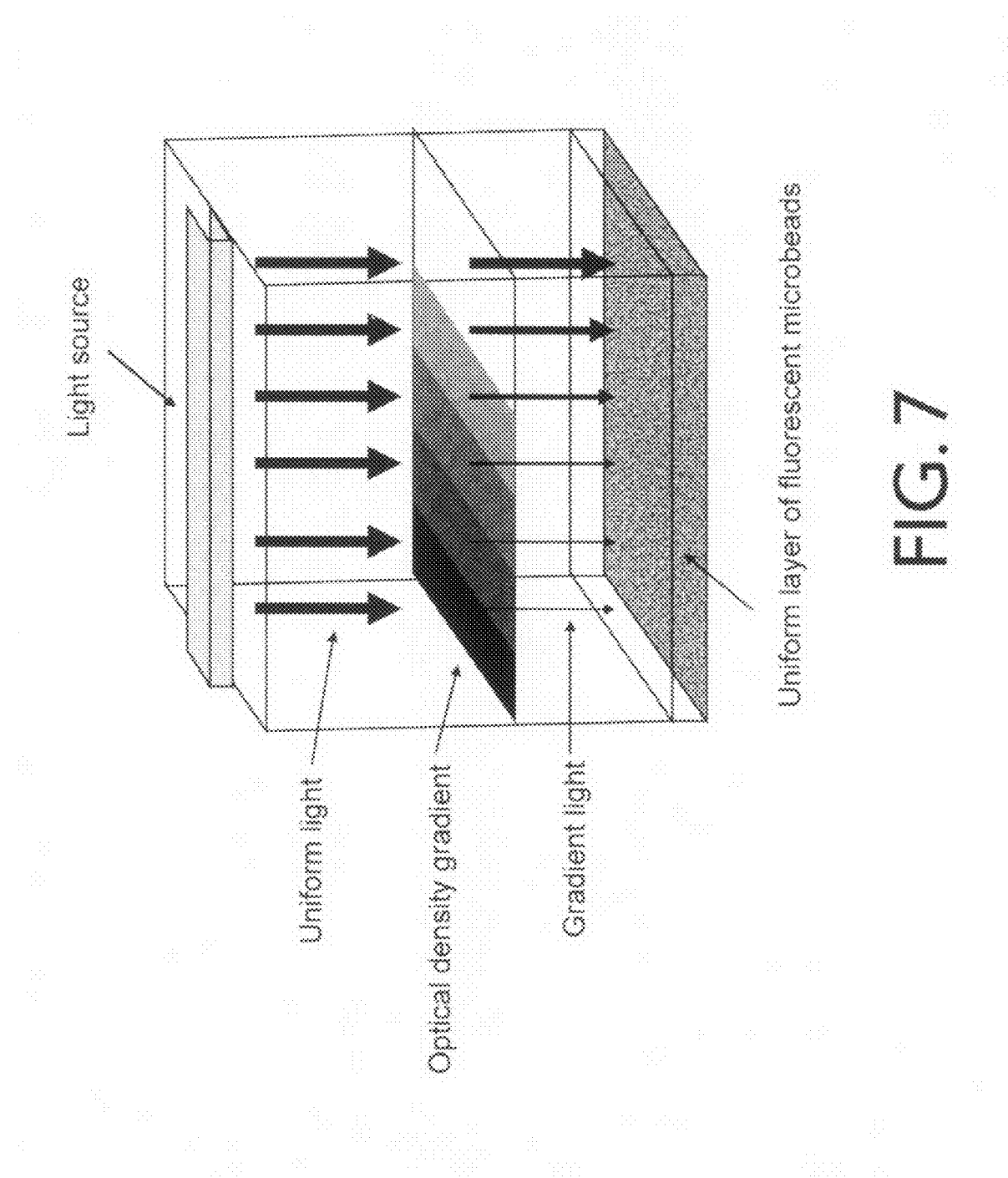
FIG. 7 shows the apparatus used to photo bleach a population of microbeads according to the present invention.

More specifically, the microbead surrogate cell standard is produced from a profile of an actual fluorescently labeled biological cell population by obtaining a list mode file from the cell population of interest with a flow cytometer. The channel number and correlated event data from the list mode file is then transferred to a spreadsheet indicating the number of events represented in each channel of the intensity scale as shown in FIG. 9. This intensity profile is then inverted by subtracting the number of events in each channel from the value in the channel with the maximum events as shown in FIG. 10. These inverted event values are then numerically sorted as shown in FIG. 11. This sorted list is then converted to a percent of the maximum value as shown in FIG. 12. These converted sorted numbers are then used to generate a density gradient as shown in FIG. 3, through which a uniform light source is directed onto a uniform layer of microbeads so that areas of the microbeads will photo bleach to a relative value inversely proportional to the density gradient covering them as shown in FIG. 6.

EXAMPLES

Example 1

Mixing Fluorescent Microbead Populations

Mix together proportions of a series fluorescence microbead populations labeled with phycoerythrin (PE) of increasingly fluorescence intensity by a factor of 0.3 decades of the same size that have wide intensity distributions, e.g., >25%. Suspend this mixture in a diluent containing 0.1% Tween 20 and run this mixture in a flow cytometer, gate on the singlet to obtain a FL2 histogram. The resulting histogram mimics the low intensity population of CD8 labeled PE lymphocytes.

Example 2

Controlling Fluorescence Intensity Distribution During Microbead Dying Procedure After swelling polymethyl methacrylate microbeads with 100% methanol, propidum iodide (PI) dissolved in methanol was introduced at the top of the microbead suspension without stirring. The PI was allowed to diffused down through the suspension while the microbeads were settling to the bottom. After 30 minutes, the methanol was decanted from the microbeads and they were re-suspended in PBS containing 0.1% Tween 20. The fluorescence intensity distribution of the microbead population was found to have a wide distribution skewed to the left, >60% CV.

Example 3

Precision Photobleaching

A highly uniform population of fluorescein-labeled microbeads was allowed to settle over an area so that the resulting microbeads formed a uniformly thick layer. Most of the suspension solution was removed so that the microbeads were covered by only a few millimeters of solution. An optical density gradient produced by applying the algorithm to a list mode histogram file from gated CD8 FITC labeled lymphocytes. This gradient was placed 5 mm above the uniform layer of microbeads and a 50 w high intensity lamp was directed onto the gradient for 2 hours so that the layer of microbeads was exposed to the resulting gradient light levels. The microbeads were then re-suspended and washed in PBS containing 0.1% Tween 20. The resulting fluorescent intensity histogram of the precision photobleached microbeads mimicked the gated CD8 FITC labeled lymphocytes While a preferred embodiment of the invention has been described in detail, it should be apparent that modifications and variations thereto are possible, all of which fall within the true spirit and scope of the invention.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present embodiment of the invention.

Therefore, the foregoing is considered as illustrative only of the principles of the embodiment of the invention. Further, since numerous modifications and changes will readily occur to those skilled in the art, it is not desired to limit the embodiment of the invention to the exact construction and operation shown and described, and accordingly, all suitable modifications and equivalents may be resorted to, falling within the scope of the embodiment of the invention.

What is claimed is:

1. A method of producing microbead populations comprising:
   providing an optical density gradient mask that represents an intensity profile of a specific biological fluorescently labeled cell population; and
   subjecting microbeads to a source of illumination through said optical density gradient mask so that an intensity profile of said microbead populations mimics the intensity profile of said specific biological fluorescently labeled cell population.

2. The method of claim 1, further comprising:
   determining the intensity profile of said specific biological fluorescently labeled cell population prior to providing said optical density gradient mask.

3. The method of claim 1, wherein the step of providing said optical density gradient mask comprises:
   obtaining a list mode file of the intensity profile of said biological fluorescently labeled cell population;
   mathematically inverting the number of events in each channel of said list mode file;
   converting the number of events in each channel to a percentile;
   sorting the percentiles; and
   generating said optical density gradient mask being proportional to said sorted percentiles; and
   uniformly depositing said optical density gradient mask on a surface.

4. The method of claim 2, wherein said surface comprises a transparent material.

5. The method of claim 3, wherein the number of events in each channel is mathematically inverted by subtracting the number of events in each channel from the number of events in the channel with the maximum amount of events.

6. The method of claim 3, wherein said percentiles are sorted in an ascending order.

7. The method of claim 3, wherein said percentiles are sorted in a descending order.

8. The method of claim 1, further comprising selectively controlling at least one of: the intensity of said source of illumination and the amount of time said source of illumination is applied.

9. The method of claim 3, wherein said list mode file is obtained from a flow cytometer.

10. A method of producing microbead populations comprising:
    providing a light source that has uniform intensity across a given area;
    providing an optical density gradient mask that represents the intensity profile of a specific biological fluorescently labeled cell population;
    allowing the illumination of said light source to pass through said optical density gradient mask onto an area of uniformly deposited microbeads.

11. The method of claim 10, wherein an intensity profile of said microbeads mimics the intensity profile of said specific biological fluorescently labeled cell population.

12. A method of producing microbead populations comprising:
    illuminating a microbead population through mask means that represents the intensity profile of a specific biological fluorescently labeled cell population, so that the intensity profile of said microbead population mimics said intensity profile of the specific biological fluorescently labeled cell population.

* * * * *